United States Patent [19]

Berg

[11] Patent Number: 5,582,693
[45] Date of Patent: Dec. 10, 1996

[54] SEPARATION OF 3-CARENE AND LIMONENE BY AZEOTROPIC DISTILLATION

[75] Inventor: Lloyd Berg, 1314 S. Third Ave., Bozeman, Mont. 59715

[73] Assignee: Lloyd Berg, Bozeman, Mont.

[21] Appl. No.: 584,983

[22] Filed: Jan. 11, 1996

[51] Int. Cl.$^6$ .............................. B01D 3/36; C07C 7/06
[52] U.S. Cl. .............................. 203/57; 203/58; 203/59; 203/60; 203/61; 203/62; 203/63; 203/64; 203/65; 203/68; 585/350; 585/860; 585/865; 585/866
[58] Field of Search .............................. 203/57, 58, 60, 203/61, 63, 62, 64, 68, 65, 59; 585/350, 862, 860, 865, 866

[56] References Cited

U.S. PATENT DOCUMENTS

| 2,459,433 | 1/1949 | Johnson et al. | 203/65 |
| 5,380,405 | 1/1995 | Berg | 203/57 |
| 5,391,264 | 2/1995 | Berg | 203/57 |
| 5,421,965 | 6/1995 | Berg | 203/58 |
| 5,423,955 | 6/1995 | Berg | 203/68 |
| 5,425,853 | 6/1995 | Berg | 203/57 |

*Primary Examiner*—Virginia Manoharan

[57] ABSTRACT

3-Carene and limonene cannot be separated from each other by rectification because of the closeness of their boiling points. They are readily separated by azeotropic distillation. Effective agents are: cyclopentanol, 2-nitropropane, ethyl formate amyl acetate dimethyl carbonate, tetrahydrofuran, acetic acid and 2-amino-amethyl-1-propanol.

1 Claim, No Drawings

SEPARATION OF 3-CARENE AND LIMONENE BY AZEOTROPIC DISTILLATION

FIELD OF THE INVENTION

This invention relates to a method of separating 3-carene, limonene and phellandrene using certain organic liquids as the agent in azeotropic distillation.

DESCRIPTION OF PRIOR ART

Azeotropic distillation is the method of separating close boiling compounds or azeotropes from each other by carrying out the distillation in a multiplate rectification column in the presence of an added liquid, said liquid forming an azeotrope with one or two of the compounds to be separated. Its presence on each plate of the rectification column alters the relative volatility in a direction to make the separation on each plate greater and thus require either fewer plates to effect the same separation or make possible a greater degree of separation with the same number of plates. The azeotrope forming agent is introduced with the feed to a continuous column. The azeotrope forming agent and the more volatile component are taken off as overhead product and the less volatile component comes off as bottoms product. The usual methods of separating the azeotrope former from the more volatile component are cooling and phase separation or solvent extraction.

The usual method of evaluating the effectiveness of azeotropic distillation agents is the change in relative volatility of the compounds to be separated. Table 1 shows the degree of separation or purity obtainable by theoretical plates at several relative volatilities. Table 1 shows that a relative volatility of at least 1.2 is required to get an effective separation by rectification.

TABLE 1

Effect of Relative Volatility on Theoretical Stage Requirements.

| Separation Purity, Both Products (Mole Fraction) | Relative Volatility | | | | | | | |
|---|---|---|---|---|---|---|---|---|
| | 1.02 | 1.1 | 1.2 | 1.3 | 1.4 | 1.5 | 2.0 | 3.0 |
| | Theoretical Stages at Total Reflux | | | | | | | |
| 0.999 | 697 | 144 | 75 | 52 | 40 | 33 | 19 | 12 |
| 0.995 | 534 | 110 | 57 | 39 | 30 | 25 | 14 | 9 |
| 0.990 | 463 | 99 | 49 | 34 | 28 | 22 | 12 | 7 |
| 0.98 | 392 | 81 | 42 | 29 | 22 | 18 | 10 | 6 |
| 0.95 | 296 | 61 | 31 | 21 | 16 | 14 | 8 | 4 |
| 0.90 | 221 | 45 | 23 | 16 | 12 | 10 | 5 | 3 |

There are a number of commercial processes which produce complex mixtures of terpenes, e.g. turpentine. A process to separate this mixture into its pure components would enhance its value. Three of the commonest close boiling compounds in one of these are 3-carene, B.P.=167° C., phellandrene, B.P.=175° C. and limonene, B.P.=178° C. The relative volatility among these three is as low as 1.05 which makes it impossible to separate by conventional rectification. Azeotropic distillation would be an attractive method of effecting the separation of these three if agents can be found that (1) will create a large apparent relative volatility among these three and (2) are easy to recover from the azeotropic agent. Table 2 shows the relative volatility required to obtain 99% purity. With an agent giving a relative volatility of 1.75, only 23 actual plates are required.

TABLE 2

Theoretical and Actual Plates Required vs. Relative Volatility for Terpene Separation

| Relative Volatility | Theoretical Plates Required At Total Reflux, 99% Purity | Actual Plates Required 75% Efficiency |
|---|---|---|
| 1.4 | 28 | 38 |
| 1.6 | 20 | 27 |
| 1.75 | 17 | 23 |

OBJECTIVE OF THE INVENTION

The object of this invention is to provide a process or method of azeotropic distillation that will enhance the relative volatility of 3-carene, limonene and phellandrene in their separation in a rectification column. It is a further object of this invention to identify organic compounds which in addition to the above constraints, are stable, can be separated from the terpenes and recycled to the column with little decomposition.

SUMMARY OF THE INVENTION

The objects of this invention are provided by a process for separating 3-carene, limonene and phellandrene which entails the use of certain organic compounds as the agent in azeotropic distillation.

DETAILED DESCRIPTION OF THE INVENTION

I have discovered that certain organic compounds will greatly improve the relative volatility between 3-carene, limonene and phellandrene and permit the by rectification when employed as the agent in azeotropic distillation. Table 3 lists the compounds that I have found to be effective in separating 3-carene from limonene in the presence of phellandrene. They are amyl acetate, ethyl acetate, acetonitrile, acetal, methyl t-butyl ether, anisole, t-amyl methyl ether, isopropyl ether, dioxolane, propyl formate, ethyl acetoacetate, methyl formate, ethyl isobutyrate, methyl propionate, methyl lactate, propyl propionate, butyl propionate,

TABLE 3

Effective Azeotropic Distillation Agents For Separating 3-Carene From Limonene and Phellandrene

| Agent | Temp., °C. | Rel. Vol. 3-Car/Lim |
|---|---|---|
| Amyl acetate | 146 | 1.75 |
| Ethyl acetate | 86 | 1.75 |
| Acetonitrile | 78 | 1.4 |
| Acetal | 112 | 1.35 |
| Methyl t-butyl ether | 70 | 1.5 |
| Anisole | 153 | 1.55 |
| t-Amyl methyl ether | 106 | 1.3 |
| Isopropyl ether | 84 | 1.4 |
| Dioxolane | 82 | 1.5 |
| Propyl formate | 91 | 1.8 |
| Ethyl acetoacetate | 158 | 1.35 |
| Methyl formate | 36 | 1.4 |
| Ethyl isobutyrate | 131 | 1.3 |
| Methyl propionate | 84 | 1.35 |
| Methyl lactate | 138 | 1.55 |
| Propyl propionate | 128 | 1.45 |
| Butyl propionate | 151 | 1.8 |
| Ethyl isovalerate | 144 | 1.35 |
| Ethyl formate | 59 | 1.55 |
| Dimethyl carbonate | 94 | 1.5 |
| 2-Butanol | 100 | 1.35 |

TABLE 3-continued

Effective Azeotropic Distillation Agents For Separating 3-Carene From Limonene and Phellandrene

| Agent | Temp., °C. | Rel. Vol. 3-Car/Lim |
|---|---|---|
| 1-Butanol | 118 | 1.45 |
| t-Amyl alcohol | 107 | 1.35 |
| n-Amyl alcohol | 134 | 1.3 |
| Cyclohexanol | 153 | 1.3 |
| 3-Pentanone | 109 | 1.4 |
| 3-Methyl-2-butanone | 108 | 1.35 |
| 2-Octanone | 165 | 1.35 |
| Butyronitrile | 118 | 1.4 |
| Triethyl amine | 106 | 1.4 |
| Ethanolamine* | 146 | 1.35 |
| Butyl amine | 91 | 1.35 |
| 2-Butanone | 82 | 1.45 |
| Acetone | 57 | 1.55 |
| Diethyl amine | 71 | 1.35 |
| Dipropyl amine | 125 | 1.3 |
| Pyridine | 123 | 1.6 |
| 2-Methoxyethanol | 121 | 1.5 |
| Diethylene glycol methyl ether | 166 | 1.3 |
| Tetrahydrofuran | 80 | 1.45 |
| Acetic acid | 115 | 1.4 |
| Butyric acid | 155 | 1.3 |
| Methyl pivalate | 108 | 1.45 |
| Methyl ethyl ketoxime | 147 | 1.3 |
| Cyclopentanol | 131 | 1.3 |
| 2-Amino-2-methyl-1-propanol | 150 | 1.3 |
| 2-Nitropropane | 120 | 1.35 |
| 2-Butoxyethanol | 159 | 1.35 |

*Two phase ethyl isovalerate, ethyl formate, dimethyl carbonate, 2-butanol, 1-butanol, t-amyl alcohol, n-amyl alcohol, cyclohexanol, 3-pentanone, 3-methyl-2-butanone, 2-octanone, butyronitrile, triethyl amine, ethanolamine, butyl amine, 2-butanone, acetone, diethyl amine, dipropyl amine, pyridine, 2-methoxyethanol, diethylene glycol methyl ether, tetrahydrofuran, acetic acid, butyric acid, methyl pivalate, methyl ethyl ketoxime, 2-amino-2-methyl-1-propanol, 2-nitropropane, 2-butoxyethanol and cyclopentanol.

Table 4 lists the compounds that are effective in separating 3-carene from limonene. They are amyl acetate, 1-butanol, anisole, isopropyl ether, dioxolane, ethyl formate, methyl acetate, methyl propionate, methyl formate, ethyl acetate, propyl propionate, n-butyl propionate, dimethyl carbonate, t-amyl alcohol, 3-pentanone, 2-octanone, 2-pentanone, 3-methyl-2-butanone, 2,3-butanedione, cyclohexanone, acetonitrile, butyronitrile, 2-butanone, diethylene glycol methyl ether, butyl amine, dipropyl amine, triethyl amine, 2-methoxyethanol, acetone, p-cresol, pyridine, tetrahydrofuran, 2,6-dimethyl phenol, propylene carbonate, 2-methyl-2,4-pentanediol, 1,1,3,3-tetramethyl urea, 4-hydroxy-4-methyl-2-pentanone, methyl ethyl ketoxime, 2-nitropropane, butyraldehyde oxime, 1,2-Methylenedioxybenzene, 1-methoxy-2-propanol, 2-amino-2-methyl-1-propanol, 2-butoxyethanol, propoxypropanol, 4-fluoro benzaldehyde and cyclopentanol.

Table 5 lists the compounds that are effective in separating phellandrene from 3-carene and limonene. They are dimethylformamide, ethyl lactate, cyclopentanol, 4-hydroxy-4-methyl-2-pentanone, formic acid, butyraldehyde oxime, 1,2-methylene dioxybenzene, 1-methoxy-2-propanol, 2-dimethylamine-2-methyl-2-propanol and 2-nitropropane.

THE USEFULNESS OF THE INVENTION

The usefulness or utility of this invention can be demonstrated by referring to the data presented in Tables 3, 4 and 5. All of the successful agents show that 3-carene, limonene and phellandrene can be separated from each other by means of azeotropic distillation in a rectification column and that the ease of separation as measured by relative volatility is considerable.

TABLE 4

Effective Azeotropic Distillation Agents For Separating 3-Carene From Limonene

| Agent | Temp., °C. | Rel. Vol. 3-Car/Lim |
|---|---|---|
| Amyl acetate | 153 | 1.65 |
| 1-Butanol | 120 | 1.55 |
| Anisole | 152 | 1.4 |
| Isopropyl ether | 91 | 1.45 |
| Dioxolane | 78 | 1.4 |
| Ethyl formate | 58 | 1.7 |
| Methyl acetate | 56 | 1.65 |
| Methyl propionate | 83 | 1.35 |
| Methyl formate | 31 | 1.75 |
| Ethyl acetate | 83 | 1.3 |
| Propyl propionate | 138 | 1.5 |
| n-Butyl propionate | 133 | 1.3 |
| Dimethyl carbonate | 92 | 1.3 |
| t-Amyl alcohol | 107 | 1.35 |
| 3-Pentanone | 119 | 1.35 |
| 2-Octanone | 162 | 1.35 |
| 3-Methyl-2-butanone | 104 | 1.35 |
| 2,3-Butanedione | 93 | 1.45 |
| 2-Pentanone | 110 | 1.4 |
| Cyclohexanone | 150 | 1.3 |
| Acetonitrile | 80 | 1.5 |
| Butyronitrile | 117 | 1.7 |
| 2-Butanone | 90 | 1.35 |
| Diethylene glycol methyl ether | 165 | 1.3 |
| Butyl amine | 86 | 1.4 |
| Dipropyl amine | 119 | 1.3 |
| Triethyl amine | 99 | 1.3 |
| 2-Methoxyethanol | 120 | 1.4 |
| Acetone | 56 | 1.5 |
| p-Cresol | 156 | 1.4 |
| Pyridine | 114 | 1.5 |
| Tetrahydrofuran | 88 | 1.4 |
| 2,6-Dimethyl phenol | 146 | 1.4 |
| 2-Methyl-2,4-pentanediol | 166 | 1.3 |
| 1,1,3,3-Tetramethyl urea | 163 | 1.35 |
| Propylene carbonate | 166 | 1.3 |
| 4-Hydroxy-4-methyl-2-pentanone | 131 | 1.55 |
| Methyl ethyl ketoxime | 145 | 1.45 |
| Cyclopentanol | 127 | 1.6 |
| Butyraldehyde oxime | 142 | 1.4 |
| 1,2-Methylene dioxybenzene | 164 | 1.3 |
| 1-Methoxy-2-propanol | 120 | 1.35 |
| 2-Amino-2-methyl-1-propanol | 147 | 1.5 |
| 2-Nitropropane | 120 | 1.55 |
| 2-Butoxyethanol | 160 | 1.3 |
| Propoxypropanol | 149 | 1.5 |
| 4-Fluoro benzaldehyde | 164 | 1.65 |

TABLE 5

Effective Azeotropic Distillation Agents For Separating Phellandrene From 3-Carene and Limonene

| Agent | Temp. °C. | Rel. Vol. Lim/Phl |
|---|---|---|
| Dimethylformamide | 127 | 1.6 |
| Ethyl lactate | 146 | 1.45 |
| Cyclopentanol | 137 | 2.0 |
| 4-Hydroxy-4-methyl-2-pentanone | 148 | 1.45 |
| Formic acid | 103 | 1.3 |
| Butyraldehyde oxime | 145 | 1.35 |
| 1,2-Methylene dioxybenzene | 164 | 1.35 |
| 1-Methoxy-2-propanol | 126 | 1.45 |
| 2-Dimethylamine-2-methyl-2-propanol | 150 | 1.8 |
| 2-Nitropropane | 120 | 1.5 |

WORKING EXAMPLES

1. One hundred grams of a crude turpentine mixture containing principally 3-carene, limonene and phellandrene and 100 grams of amyl acetate were charged to the stillpot of five theoretical plate glass perforated plate rectification column and operated at total reflux for nine hours. The overhead composition was 94% 3-carene, 4% limonene and 2% phellandrene; the stillpot composition was 48% 3-carene, 32.1& limonene and 19.9% phellandrene. This indicates a relative volatility of 3-carene to limonene of 1.65 and limonene to phellandrene of 1.04.

2. Twenty grams of 3-carene, 80 grams of limonene and 100 grams of cyclopentanol were charged to the five theoretical plate perforated plate rectification column and operated at total reflux for nine hours. The overhead composition was 74.9% 3-carene, 25.1% limonene; the stillpot composition was 21.6% 3-carene, 78.4% limonene. This indicates a relative volatility of 1.6.

3. One hundred grams of the crude turpentine mixture of 3-carene, limonene and phellandrene and 100 grams of dimethylformamide were charged to the five theoretical plate rectification column and refluxed for nine hours. The overhead composition was 88.9% 3-carene, 8.3% limonene and 2.8% phellandrene; the stillpot composition was 51.6% 3-carene, 13.7% limonene and 34.7% phellandrene. This indicates a relative volatility of 3-carene to limonene of 1.24 and of limonene to phellandrene of 1.5.

I claim:

1. A method for recovering 3-carene from a mixture consisting of 3-carene and limonene which consists essentially of distilling said mixture consisting of 3-carene and limonene in the presence of an azeotrope forming agent, recovering the 3-carene and the azeotrope forming agent as overhead product and obtaining the limonene as bottoms product, wherein said azeotrope forming agent consists of one material selected from the group consisting of cyclopentanol, 2-nitropropane, 2-butoxyethanol, amyl acetate, ethyl acetate, acetonitrile, acetal, methyl t-butyl ether, anisole, t-amyl methyl ether, isopropyl ether, dioxolane, propyl formate, ethyl acetoacetate, methyl formate, ethyl isobutyrate, methyl propionate, methyl lactate, propyl propionate, butyl propionate, ethyl isovalerate, ethyl formate, dimethyl carbonate, 2-butanol, 1-butanol, t-amyl alcohol, n-amyl alcohol, cyclohexanol, 3-pentanone, 3-methyl-2-butanone, 2-octanone, butyronitrile, triethyl amine, ethanolamine, butyl amine, 2-butanone, acetone, diethyl amine, dipropyl amine, pyridine, 2-methoxyethanol, diethylene glycol methyl ether, tetrahydrofuran, acetic acid, butyric acid, methyl pivalate, methyl ethyl ketoxime and 2-amino-2-methyl-1-propanol.

* * * * *